(12) United States Patent
Humfeld et al.

(10) Patent No.: US 11,703,472 B2
(45) Date of Patent: Jul. 18, 2023

(54) SYSTEMS AND METHODS FOR ACCELERATED CONDITIONING OF COMPOSITE CORE SANDWICH COUPONS

(71) Applicant: The Boeing Company, Chicago, IL (US)

(72) Inventors: Keith D. Humfeld, Chicago, IL (US); Joseph A. Bolton, Chicago, IL (US)

(73) Assignee: The Boeing Company, Chicago, IL (US)

( * ) Notice: Subject to any disclaimer, the term of this patent is extended or adjusted under 35 U.S.C. 154(b) by 782 days.

(21) Appl. No.: 16/712,303

(22) Filed: Dec. 12, 2019

(65) Prior Publication Data
US 2021/0181133 A1    Jun. 17, 2021

(51) Int. Cl.
| | |
|---|---|
| *G01N 25/58* | (2006.01) |
| *G01N 17/00* | (2006.01) |
| *G01N 25/56* | (2006.01) |
| *G01N 33/00* | (2006.01) |

(52) U.S. Cl.
CPC .......... *G01N 25/58* (2013.01); *G01N 17/002* (2013.01); *G01N 25/56* (2013.01); *G01N 2033/0083* (2013.01)

(58) Field of Classification Search
CPC ...... G01N 25/58; G01N 25/56; G01N 17/002; G01N 2033/0083
See application file for complete search history.

(56) References Cited

U.S. PATENT DOCUMENTS

2015/0260637 A1    9/2015   Iannone

FOREIGN PATENT DOCUMENTS

| EP | 3 553 438 | 10/2019 |
|---|---|---|
| RU | 2616438 | 4/2017 |

OTHER PUBLICATIONS

Radtke, T.C. et al. "Hot/Wet Environmental Degradation of Honeycomb Sandwich Structure Representative of F/A-18: Flatwise Tension Strength" DSTO Aeronautical and Maritime Research Laboratory, Sep. 1999. (Year: 1999).*

(Continued)

*Primary Examiner* — Paul M. West
(74) *Attorney, Agent, or Firm* — McDonnell Boehnen Hulbert & Berghoff LLP

(57) ABSTRACT

In an example, a method for accelerated conditioning of a composite core sandwich coupon is described. The method includes setting a first temperature and a first relative humidity level of the conditioning apparatus, wherein a combination of the first temperature and the first relative humidity level correspond to a desired relative humidity level of the plurality of cells of the core layer at room temperature. The method includes maintaining the first temperature and the first relative humidity for a first period, wherein during the first period a core humidity of the plurality of cells in the core layer approaches the first relative humidity level. The method includes determining that the core humidity has reached the first relative humidity level. The method includes, based on determining that the core humidity has reached the first relative humidity level, adjusting the first temperature to a second temperature.

20 Claims, 8 Drawing Sheets

(56) References Cited

OTHER PUBLICATIONS

Mark E. Tuttle, "Moisture Ingression in Honeycomb Sandwich Composites Due to Exposure to Humidity", Sampe Conf. Proceedings; AMPE 2010, Conf. and Exhibition "New Materials and Processes for a New Economy", Society for the Advancement of Material and Process Engineering Markets and Evolving Technologies, Long Beach, CA, Jan. 1, 2010, pp. 1-12.

Jedi Rosero Alvarado, "Etude de 1 effect d un traitement ignfigue de de 1 orientation du fil du bois sur la formation de la pelure d orange des panneaux sandwich decoratifs". Thesis, Dec. 31, 2017, Universite Laval, retrieved from internet: https://corpus.ulaval.ca/jspui/bitstream/20.500.11794/27814/1/33838.pdf, English abstract included.

Extended European Search Report prepared by the European Patent Office in application No. EP 20 21 3464, dated May 7, 2021.

Maximum Moisture Carrying Capacity of Air: https://www.engineeringtoolbox.com/maximum-moisture-content-air-d_1403.html.

Pathak et al., "Effects of Moisture Diffusion in Sandwich Composite Structures", Joint Advanced Materials & Structures Center of Excellence, 2018.

Vodicka, "Accelerated Environmental Testing of Composite Materials", Department of Defence, Apr. 1998.

\* cited by examiner

SYSTEMS AND METHODS FOR ACCELERATED CONDITIONING OF COMPOSITE CORE SANDWICH COUPONS

FIELD

The present disclosure relates generally to accelerated conditioning of materials. In particular, the present disclosure relates to accelerating conditioning of composite core sandwich coupons.

BACKGROUND

Prior to incorporating materials into a system that has an expected useful lifetime, such as an aircraft, it is important to ensure that those materials will maintain a benchmark level of performance at least throughout the expected useful lifetime. This may involve subjecting such materials to conditions anticipated to be experienced during operations of the system.

However, if the system has an expected useful length that is several years long, it may be impractical to wait for this same period of time to test the materials. In particular, the time taken to test the materials may be longer than the time it takes to develop potentially improved materials, and applicable standards may change during this period. Accordingly, testing materials for the full expected useful lifetime of the system is often ineffective. Existing ways of accelerating conditioning of materials to allow for quicker incorporation into systems still can take months or years. In particular, incorporating moisture into certain materials, such as composite core materials, can take undue amounts of time What is needed is a system for accelerated conditioning of composite core materials that quickly and reliably conditions these materials.

SUMMARY

In an example, a method for accelerated conditioning of a composite core sandwich coupon within a conditioning apparatus is provided. The composite core sandwich coupon includes (i) an outer composite layer, and (ii) an inner core layer, and wherein the core layer comprises a plurality of cells. The method includes setting, at a first time by a controller of the conditioning apparatus, a first temperature and a first relative humidity level of the conditioning apparatus, wherein the first temperature is above room temperature, and wherein a combination of the first temperature and the first relative humidity level correspond to a desired relative humidity level of the plurality of cells of the core layer at room temperature. The method includes maintaining, by the controller, the first temperature and the first relative humidity for a first period, wherein during the first period a core humidity of the plurality of cells in the core layer approaches the first relative humidity level. The method includes determining that the core humidity has reached the first relative humidity level. The method includes, based on determining that the core humidity has reached the first relative humidity level, adjusting, at a second time by the controller of the conditioning apparatus, the first temperature to a second temperature, wherein the second temperature is between the first temperature and room temperature, and wherein, responsive to adjusting the first temperature to the second temperature, the outer composite layer absorbs moisture from the inner core layer to approach the desired humidity level.

In another example, a system for accelerated conditioning of a composite core sandwich coupon is provided. The system includes a conditioning apparatus having a chamber configured to contain a composite core sandwich coupon, wherein the composite core sandwich coupon comprises (i) an outer composite layer, and (ii) an inner core layer, and wherein the core layer comprises a plurality of cells. The system includes a humidifier configured to provide water vapor to the chamber of the conditioning apparatus. The system includes a heater configured to provide heat to the chamber of the conditioning apparatus. The system includes a computing device comprising a processor and a memory having instructions executable by the processor to perform a set of functions, the set of functions. The set of functions includes controlling the heater to set a first temperature of the conditioning apparatus controlling the humidifier to set a first relative humidity level of the conditioning apparatus, wherein the first temperature is above room temperature, and wherein a combination of the first temperature and the first relative humidity level correspond to a desired relative humidity level of the plurality of cells of the core layer at room temperature. The set of functions includes controlling the heater to maintain the first temperature and controlling the humidifier to maintain the first relative humidity for a first period, wherein during the first period a core humidity of the plurality of cells in the core layer approaches the first relative humidity level. The set of functions includes determining that the core humidity has reached the first relative humidity level. The set of functions includes, based on determining that the core humidity has reached the first relative humidity level, causing the heater to adjust, at a second time, the first temperature to a second temperature, wherein the second temperature is between the first temperature and room temperature, and wherein, responsive to adjusting the first temperature to the second temperature, the outer composite layer absorbs moisture from the inner core layer to approach the desired humidity level.

In another example, a non-transitory computer readable medium is described. The computer readable medium has stored thereon instructions, that when executed by one or more processors of a computing device, cause the computing device to perform functions for accelerated conditioning of a composite core sandwich coupon within a conditioning apparatus. The composite core sandwich coupon comprises (i) an outer composite layer, and (ii) an inner core layer, and wherein the core layer comprises a plurality of cells. The functions include setting, at a first time by a controller of the conditioning apparatus, a first temperature and a first relative humidity level of the conditioning apparatus, wherein the first temperature is above room temperature, and wherein a combination of the first temperature and the first relative humidity level correspond to a desired relative humidity level of the plurality of cells of the core layer at room temperature. The functions include maintaining, by the controller, the first temperature and the first relative humidity for a first period, wherein during the first period a core humidity of the plurality of cells in the core layer approaches the first relative humidity level. The functions include determining that the core humidity has reached the first relative humidity level. The functions include, based on determining that the core humidity has reached the first relative humidity level, adjusting, at a second time by the controller of the conditioning apparatus, the first temperature to a second temperature, wherein the second temperature is between the first temperature and room temperature, and wherein, responsive to adjusting the first temperature to the second temperature, the outer composite layer absorbs moisture from the inner core layer to approach the desired humidity level.

The features, functions, and advantages that have been discussed can be achieved independently in various examples or may be combined in yet other examples. Further details of the examples can be seen with reference to the following description and drawings.

BRIEF DESCRIPTION OF THE FIGURES

The novel features believed characteristic of the illustrative examples are set forth in the appended claims. The illustrative examples, however, as well as a preferred mode of use, further objectives and descriptions thereof, will best be understood by reference to the following detailed description of an illustrative example of the present disclosure when read in conjunction with the accompanying drawings, wherein:

DETAILED DESCRIPTION

Figure 1:
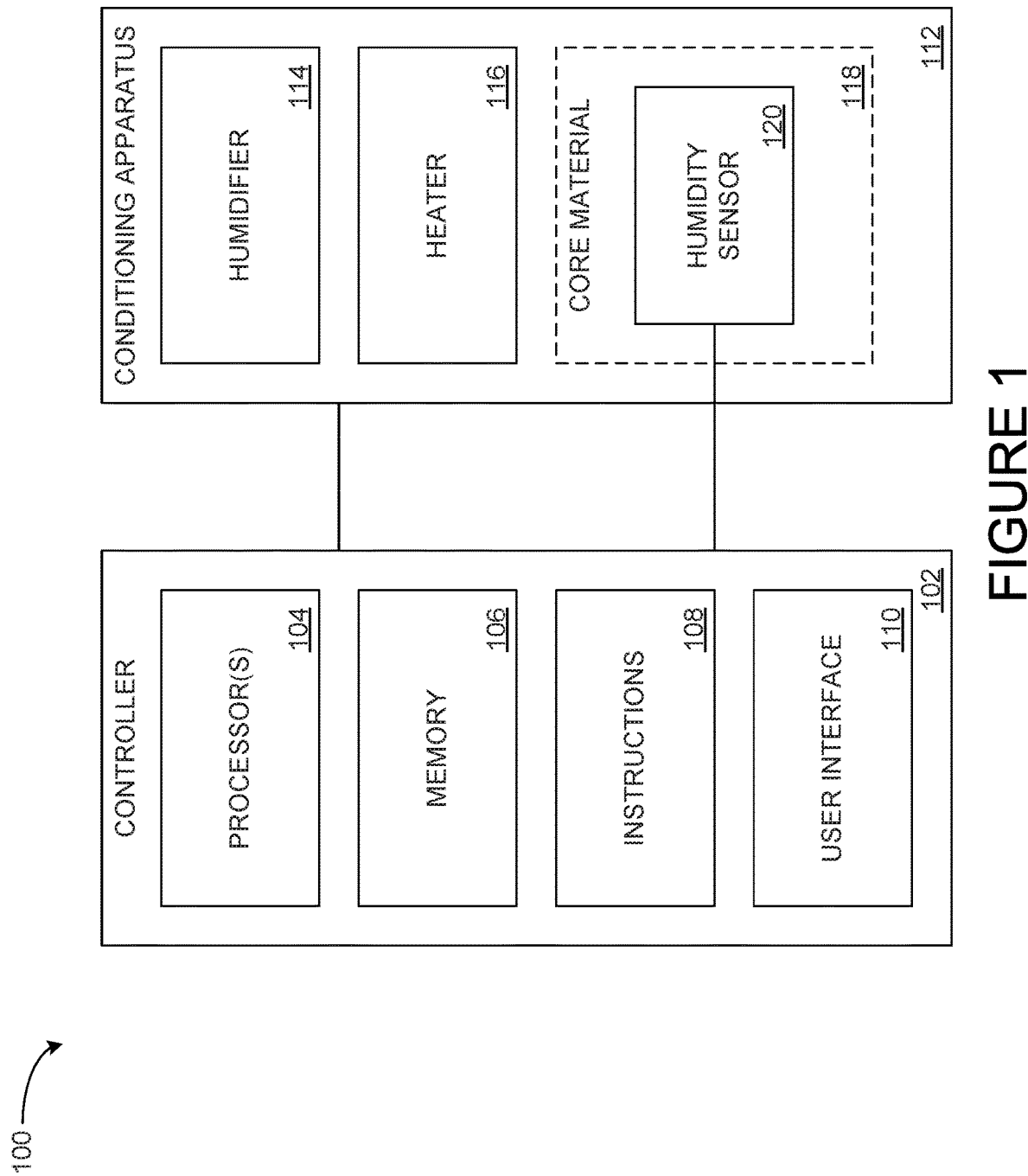
FIG. 1 illustrates a block diagram of a system for accelerated conditioning of a composite core sandwich coupon, according to an example implementation.

Disclosed examples will now be described more fully hereinafter with reference to the accompanying drawings, in which some, but not all of the disclosed examples are shown. Indeed, several different examples may be described and should not be construed as limited to the examples set forth herein. Rather, these examples are described so that this disclosure will be thorough and complete and will fully convey the scope of the disclosure to those skilled in the art.

Within examples, systems and methods for accelerating conditioning of a composite core sandwich coupon are described. These systems and methods correspond to humidity qualities of a composite material. Such composite materials are commonly used in aircraft, and typically a primary way of conditioning such materials is to artificially introduce humidity so that a composite core reaches a humidity level expected in similar materials after being used throughout the expected useful life of an aircraft. Because a composite core is often paper-based, relatively high moisture levels can significantly impact the compressive strength of the material. Accordingly, it is important to accurately condition the composite material to the humidity level expected at the end of the useful life of the aircraft (e.g., 40 years). For example, conditioning a material at a humidity level above this expected humidity level may result in over-engineering and wasted resources.

A composite coupon may include a plurality of layers, with different material types. For example, the coupon can include a first outer layer (e.g., a top facesheet) of a first material type (e.g., a composite material that includes multiple material types), a core layer of a second material type (e.g., a paper-based material) disposed below the first outer layer, and a second outer layer (e.g., a bottom facesheet) of the first material type disposed below the core layer. The outer layers may be composed of a composite material and the core material may be paper-based, aluminum, or another relatively light material. The core material may be more porous and lighter than the outer layers, but can be arranged to maximize compressive strength of the material when sandwiched between the outer layers. For example, the core material may be arranged in a honeycomb configuration having cell walls that run perpendicular to the outer layers. Due to this configuration and material properties, the core material may be more absorbent than the outer layers.

Testing a composite material in this manner generally involves taking a coupon of that material and subjecting it to certain stresses as part of a conditioning process, then determining performance-related qualities of the material after conditioning. To account for different moisture absorbency properties of the outer layers and core materials, example systems and methods involve pre-conditioning to reach a desired humidity level for the core material, then further conditioning to reach the desired humidity level for the outer layers. In these examples, a humidity sensor may be embedded directly into the core material to ensure that conditioning modes are switched precisely when the desired humidity level of the core material has been reached. In this manner, over-saturating the core material with relatively high humidity levels can be avoided.

Part of the time delay in composite core sandwich coupon conditioning involves a delay in humidity reaching the core material through the outer layers. Accordingly, within further examples, the conditioning process can be expedited by introducing holes into the outer layers that facilitate expedited humidity absorption by the core material. The holes can be drilled in a manner that does not materially impact the strength of the composite core sandwich material for later testing purposes. In related examples, the holes can be drilled, water injected, and the holes filled to further expedite humidity dispersion.

Within examples a magnetic field can be applied to further expedite humidity absorption by the core material. For example, a strong electromagnet can be implemented having magnetic field lines that run parallel to the cell walls of the core material, which promotes progression of water through the core material.

Examples described herein relate to a relative humidity level within an enclosure of a conditioning apparatus. It is understood that the saturation moisture content of air changes with temperature. Thus, within examples described herein, a "relative humidity level" refers to a humidity level relative to a maximum humidity level associated with the saturation moisture content of air at a given temperature. This relative level of humidity can be represented as a percentage.

Turning now to the figures, FIG. 1 illustrates a block diagram of a system 100 for accelerated conditioning of a composite core sandwich coupon, according to an example implementation. In particular, FIG. 1 shows a controller 102 configured to control a conditioning apparatus 112. The controller 102 can generally be understood or referred to as a computing device capable of performing functions. Though the controller 102 is depicted as being separate from the conditioning apparatus, and thus the same controller could control several different apparatuses, in some examples the controller 102 may be integrated into the conditioning apparatus 112.

The controller 102 includes one or more processor(s) 104, a memory 106, instructions 108, and a user interface 110. The one or more processor(s) 104 may be general-purpose processors or special purpose processors (e.g., digital signal processors, application specific integrated circuits, etc.). The one or more processor(s) 104 can be configured to execute the instructions 108 (e.g., computer-readable program instructions) that are stored in the memory 106 and are executable to provide the functionality of controller 102, and related systems and methods described herein.

The memory 106 may include or take the form of one or more computer-readable storage media that can be read or accessed by the processor(s) 104. The computer-readable storage media can include volatile and/or non-volatile storage components, such as optical, magnetic, organic or other memory or disc storage, which can be integrated in whole or in part with the processor(s) 104. The memory 106 is considered non-transitory computer readable media. In some examples, the memory 106 can be implemented using a single physical device (e.g., one optical, magnetic, organic or other memory or disc storage unit), while in other examples, the memory 106 can be implemented using two or more physical devices. The memory 106 thus is a non-transitory computer readable storage medium, and instructions 108 executable by the processor(s) 104 are stored on the memory 106. The instructions 108 include computer executable code.

The user interface 110 may include or take the form of a keyboard, a mouse, a touchscreen, a microphone, a gesture recognition system, a combination thereof, or another means of receiving user input by the controller 102. The user interface can be integrated into the computing device 102 as depicted in FIG. 1 or be included in another subsystem or device. Though the examples below are generally described as pertaining to use of a touchscreen, other interfaces are possible.

The conditioning apparatus 112 may include a sealable enclosure configured for holding a composite core sandwich coupon for a period of time and for maintaining consistent conditions therein. The enclosure may be large enough to hold a range of sizes of coupons. For example, a typical coupon for aircraft testing can be about three feet wide by three feet deep, and be about one inch thick. The size of a coupon can vary depending on a type of testing performed. For example, a 3'×3' coupon can be used for Large Notch Testing, a 12"×0.5" coupon can be used for double cantilever beam (DCB) testing, and a 4"×6" coupon can be used for surface testing. Different coupon sizes can be used depending on context and testing constraints. The enclosure may have a buffer in each direction, and can include a platform to allow the bottom of the coupon to be exposed to conditioning. Sizes of the enclosure and coupons may vary depending on the type of application and the material to be tested. As shown in FIG. 1, the conditioning apparatus 112 includes a humidifier 114 and a heater 116. The humidifier 114 is configured to provide the enclosure with a precise level of humidity and the heater 116 is configured to raise the heat level of the enclosure. Though not depicted, a heat sink may be included to rapidly reduce the temperature of the enclosure. Also shown in the conditioning apparatus is a core material 118, which can be understood as being the core of a composite core sandwich coupon, and a humidity sensors 120, which provides a feedback signal to the controller 102 indicative of humidity uptake progress of the core material.

As described in greater detail below, the instructions 108 may be executed by the processor(s) 104 to receive inputs from the user interface 110 indicative of the configuration and makeup of the composite core sandwich coupon. For example, thicknesses and materials of each layer may be provided, as well as a desired expected lifetime of the material, which will determine the desired humidity level. In other examples, the desired humidity level may be provided as well. Still further, a pre-conditioning characteristic of the composite core sandwich coupon may be provided as well. For example, a user may input whether the outer layers have holes drilled to promote humidity uptake. Responsive to these inputs, the controller 102 may control the conditioning apparatus 112 to subject to composite core sandwich coupon to different heat levels and humidity levels to reach the desired humidity level in both the core material and the composite outer layers.

A relative humidity level can be used for conditioning the composite core sandwich structure. The relative humidity corresponds to a percentage of the maximum amount of humidity that a medium (e.g., air) can hold at a certain temperature. Because air can hold more water as temperature increases, the same overall amount of moisture in the air may correspond to a lower relative humidity at a higher temperature than it does for a lower temperature. Accordingly, the controller 102 can set a first temperature in the conditioning apparatus to, for example, about 160 degrees Fahrenheit and control the humidifier to set the first relative humidity level to about 7%. This may correspond to a relative humidity of about 85% at room temperature. The 85% humidity level can be a desired humidity level of the core material at room temperature. However, due to the increased energy associated with increasing the temperature, the core can uptake humidity at a higher rate without becoming oversaturated.

The controller 102 can control the heater 116 to maintain the first temperature and control the humidifier 114 to maintain the first relative humidity for a first period, during which a core humidity of the plurality of cells in the core layer approaches the first relative humidity level of 7%.

The controller 102 may use feedback from the humidity sensor 120 or rely on a predetermined elapsed timeframe to determined that the core humidity has reached the first relative humidity level of 7%. Then, based on determining that the core humidity has reached the first relative humidity level, the controller 102 can cause the heater 116 to adjust the first temperature to a second temperature is between the first temperature (i.e., 160 degrees Fahrenheit) and room temperature. As the controller 102 reduces the temperature, the outer layer of the composite core sandwich structure absorbs moisture from the inner core layer and from the enclosure to approach the desired humidity level. In this manner, absorption of moisture into the composite material of the outer layer can be expedited by allowing for absorption from two directions. Further description of methods and functions of conditioning a composite core sandwich structure are provided below.

Figure 2A:
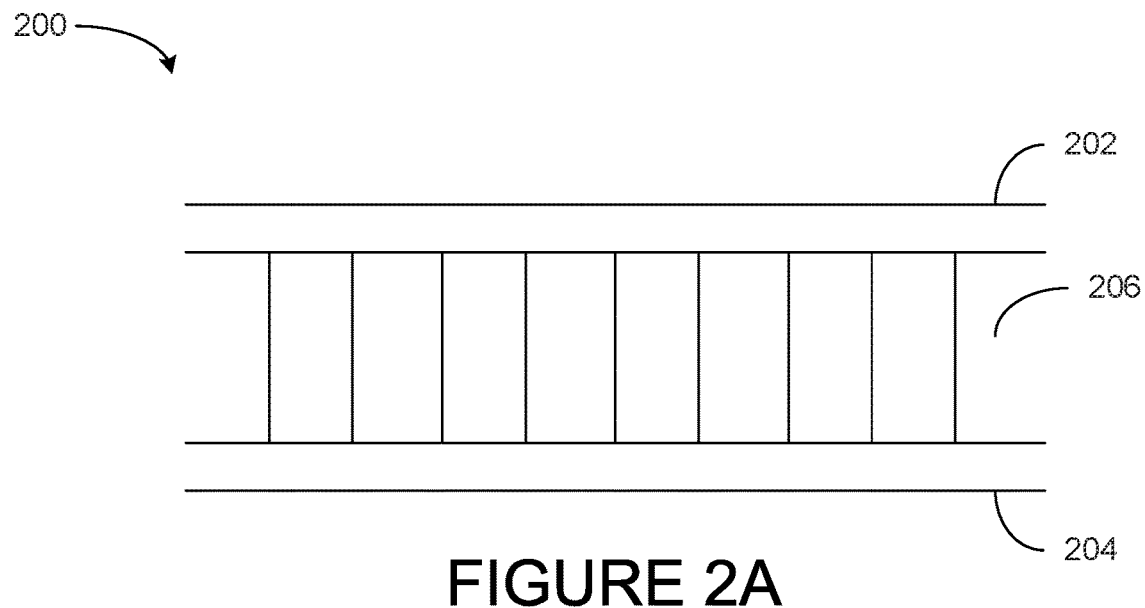
FIG. 2A illustrates a side view of a composite core sandwich coupon, according to an example implementation.

FIG. 2A illustrates a side view of a composite core sandwich coupon 200, according to an example implementation. In particular, FIG. 2A shows a cross-sectional view of the composite core sandwich coupon 200. The composite core sandwich coupon 200 includes a first outer layer 202, a second outer layer 204, and a core layer 206. The first outer layer 202 and the second outer layer 204 are outer layers, which can be composed of a composite material formed using two or more different materials, such as a carbon fiber reinforced polymer (CFRP) or a glass fiber reinforced polymer (GFRP). The core layer 206 can be formed of a paper-based material configured to maximize compressive strength when sandwiched between the outer layers. These different materials have different moisture uptake qualities, which affect how rapidly they absorb humidity when being conditioned. Further, the core layer 206 being sandwiched between the outer layers 202 and 204 affects how rapidly it absorbs moisture. Accordingly, determining an expected time period for conditioning the composite core sandwich coupon 200 may be determined based on known moisture absorption characteristics associated with each material, thicknesses of each material, and how the materials are configured.

Figure 2B:
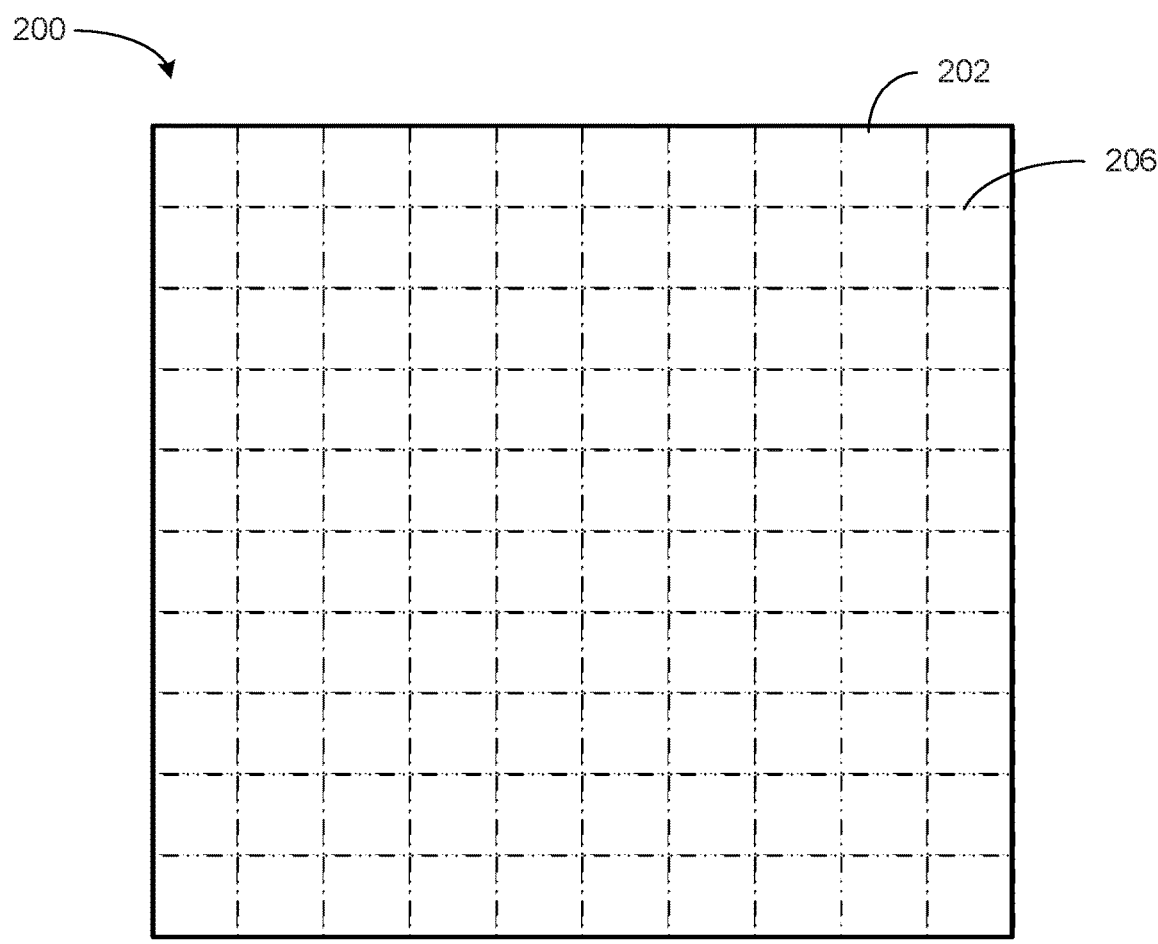
FIG. 2B illustrates a top view of a composite core sandwich coupon, according to an example implementation.

FIG. 2B illustrates a top view of the composite core sandwich coupon 200, according to an example implementation. In particular, FIG. 2B shows that the core layer 206 includes a plurality of cells. The plurality of cells have cell walls oriented perpendicularly to the first outer layer 202 and the second outer layer 204. If the composite core sandwich coupon 200 is over conditioned, rather than the moisture absorbing directly into the core material (i.e., the cell walls), the cells themselves may fill with water. This may significantly reduce the compressive strength of the core material while simultaneously increasing its weight, and this may result in a coupon that performs worse during the testing phase than it actually would if integrated into an aircraft for the expected useful lifespan of the aircraft. Accordingly, conditioning the composite core sandwich coupon 200 appropriately allows for more reliable and predictable performance of an aircraft (or any other system) that incorporates this material.

Though FIG. 2B shows the cells of core layer 206 being square-shaped, other configurations, such as a hexagonal, octagonal, or a triangular configuration, are possible. These configurations may impact moisture uptake properties of the core layer by altering the proportion of material to air in the core layer 206.

Figure 3:
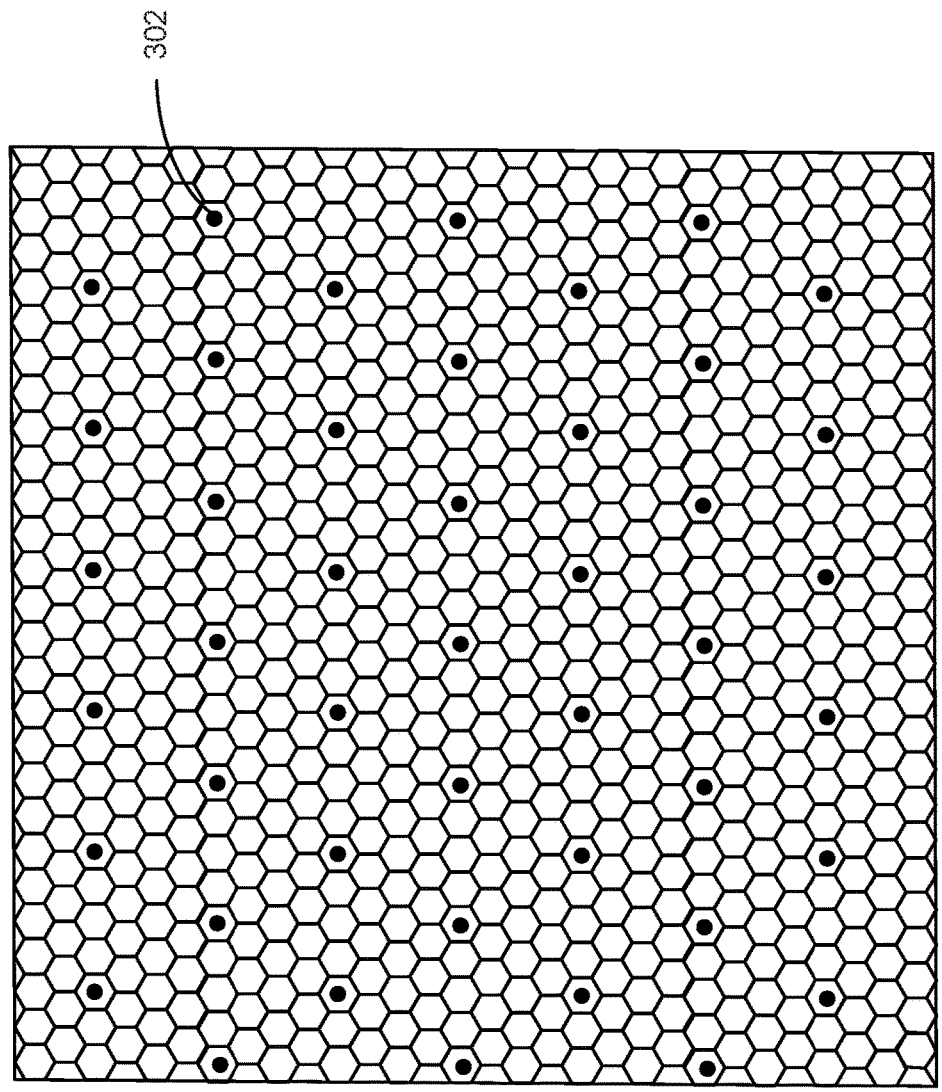
FIG. 3 illustrates a top view of a composite core sandwich coupon, according to an example implementation.

FIG. 3 illustrates a top view of a composite core sandwich coupon 300, according to an example implementation. In particular, FIG. 3 shows a plurality of holes 302. The holes have relatively small diameters (e.g., each diameter can be less than 1% as wide as a cell of the core layer) and are spaced (e.g., each hole can be spaced at least three cells from the closest adjacent pinhole) such that time taken for conditioning the composite core sandwich coupon 300 is reduced while, after conditioning, performance of the composite core sandwich coupon 300 is minimally impacted. Based on the configuration of layers in the composite core sandwich coupon 300, the computing device can set the diameter of the holes 302 and spacing between adjacent holes. In other examples, the holes 302 may be determined according to a predetermined pattern.

For example, a drilling apparatus may controlled by a computing device to create the holes 302 through the composite layer covering the core layer. The computing device can control the drilling apparatus to drill a predetermined pattern of holes through the composite layer. This may result in reducing the how long conditioning takes based on the predetermined pattern of holes by accelerating absorption of moisture into the core layer.

Within further examples, conditioning the composite core sandwich coupon 300 may further include injecting holes with water and sealing the holes. The injected water may effectively become absorbed while conditioning the composite core sandwich coupon 300 and thereby further reduce the time taken to condition the composite core sandwich coupon 300.

Figure 4:
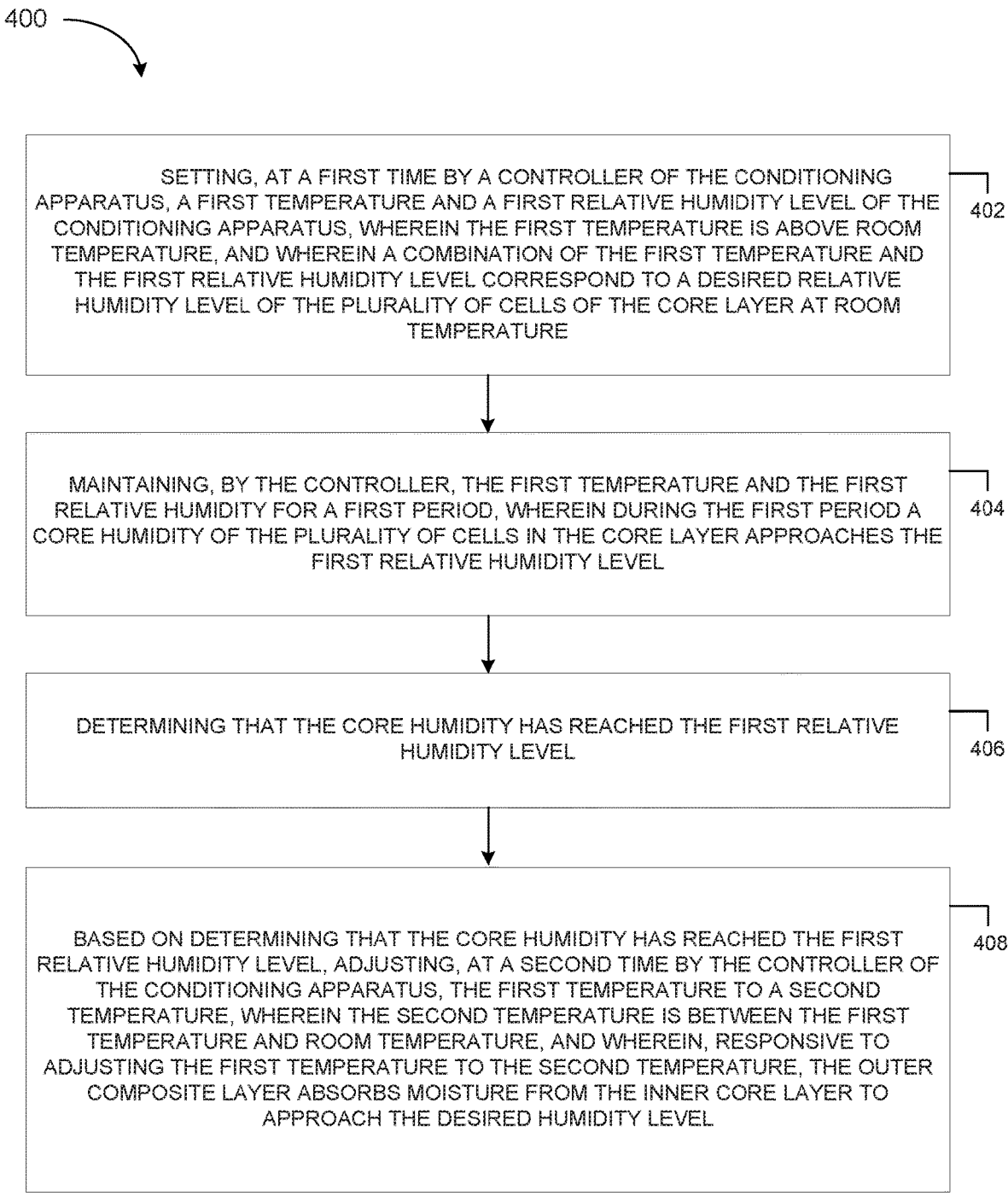
FIG. 4 illustrates a flowchart of a method for optimizing energy loading in airline operations, according to an example implementation.

FIG. 4 illustrates a flowchart of a method 400 for optimizing energy loading in airline operations, according to an example implementation. Method 400 shown in FIG. 4 presents an example of a method that could be used with the system 100 shown in FIG. 1, the composite core sandwich coupon 200 shown in FIG. 2, the composite core sandwich coupon 300 shown in FIG. 3, a combination thereof or with components of thereof. Further, the functions described with respect to FIG. 4 may be supplemented by, replaced by, or combined with functions described above with respect to FIGS. 1, 2, and 3. Further, devices or systems may be used or configured to perform logical functions presented in FIG. 4.

In some instances, components of the devices and/or systems may be configured to perform the functions such that the components are actually configured and structured (with hardware and/or software) to enable such performance. In other examples, components of the devices and/or systems may be arranged to be adapted to, capable of, or suited for performing the functions, such as when operated in a specific manner. Method 400 may include one or more operations, functions, or actions as illustrated by one or more of blocks 402-408. Further, blocks 410-444 of the method 400 may be performed in accordance with one or more of blocks 402-408. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

It should be understood that for this and other processes and methods disclosed herein, flowcharts show functionality and operation of one possible implementation of present examples. In this regard, each block or portions of each block may represent a module, a segment, or a portion of program code, which includes one or more instructions executable by a processor for implementing specific logical functions or steps in the process. The program code may be stored on any type of computer readable medium or data storage, for example, such as a storage device including a disk or hard drive. Further, the program code can be encoded on a computer-readable storage media in a machine-readable format, or on other non-transitory media or articles of manufacture. The computer readable medium may include non-transitory computer readable medium or memory, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a tangible computer readable storage medium, for example.

In addition, each block or portions of each block in FIG. 4, and within other processes and methods disclosed herein, may represent circuitry that is wired to perform the specific logical functions in the process. Alternative implementations are included within the scope of the examples of the present disclosure in which functions may be executed out of order from that shown or discussed, including substantially concurrent or in reverse order, depending on the functionality involved, as would be understood by those reasonably skilled in the art.

The method 400 relates to accelerated conditioning of a composite core sandwich coupon 200 within a conditioning apparatus 112. The composite core sandwich coupon 200 includes an outer composite layer (e.g., the first outer layer 202) and an inner core layer (e.g., the core layer 206), and the core layer includes a plurality of cells. At block 402, the method 400 include setting, at a first time by a controller 102 of the conditioning apparatus 112, a first temperature (e.g., 160 degrees Fahrenheit) and a first relative humidity level (e.g., 7%) of the conditioning apparatus 112. Within examples, the first temperature is above room temperature, and a combination of the first temperature and the first relative humidity level correspond to a desired relative humidity level (e.g., 85%) of the plurality of cells of the core layer at room temperature. The controller 102 may carry this out by controlling a heater 116 and a humidifier 114 incorporated into the conditioning apparatus 112.

At block 404, the method 400 includes maintaining, by the controller 102, the first temperature and the first relative humidity for a first period. For example, the first period may be a predetermined amount of time associated with the inner core layer reaching the first relative humidity level, or be associated with a feedback signal from the humidity sensor 120. During the first period, a core humidity of the plurality of cells in the inner core layer approaches the first relative humidity level.

At block 406, the method 400 includes determining that the core humidity has reached the first relative humidity level. For example, the inner core layer may reach 7% relative humidity after a period of time that corresponds to the materials in the composite core sandwich coupon 200 and the configuration thereof (e.g., thicknesses of layers).

At block 408, the method 400 includes, based on determining that the core humidity has reached the first relative humidity level, adjusting, at a second time by the controller 102 of the conditioning apparatus 112, the first temperature to a second temperature. The second temperature is between the first temperature and room temperature. For example, the controller 102 may cause the heater 116 iteratively reduce the temperature and correspondingly cause the humidifier 114 to increase the relative humidity to trend towards the desired humidity level at room temperature. Responsive to adjusting the first temperature to the second temperature, the outer composite layer absorbs moisture from the inner core layer to approach the desired relative humidity level. Further, within examples, the outer composite layer may also absorb moisture from an enclosure of the conditioning apparatus 112 such that the outer composite layer absorbs moisture from two directions during the second period.

Figure 5:
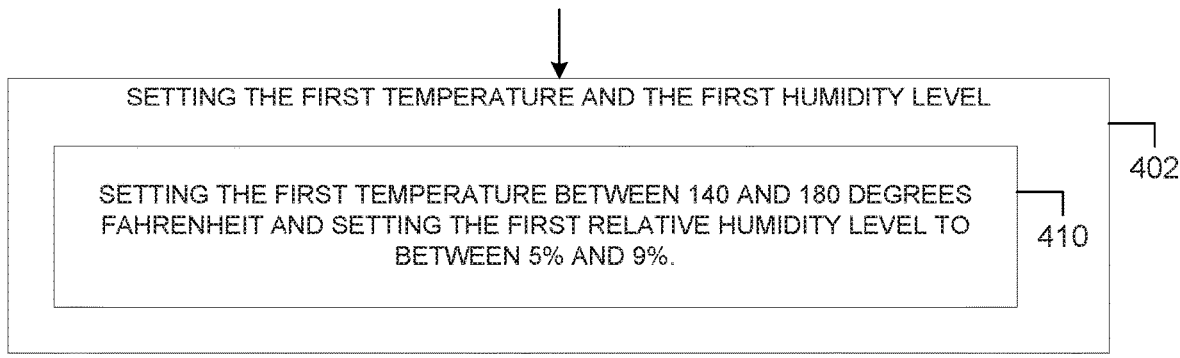
FIG. 5 illustrates a flowchart of a method for use with the method shown in FIG. 4, according to an example implementation.

FIG. 5 illustrates a flowchart of a method for use with the method 400 shown in FIG. 4, according to an example implementation. In particular, FIG. 5 illustrates the method 400 including block 410. Block 410 is performed in accordance with block 402. At block 410, the method 400 includes setting the first temperature between 140 and 180 degrees Fahrenheit and setting the first relative humidity level to between 5% and 9%. For example, the first temperature can be around 160 degrees Fahrenheit and the first relatively humidity level can be around 7%.

Figure 6:
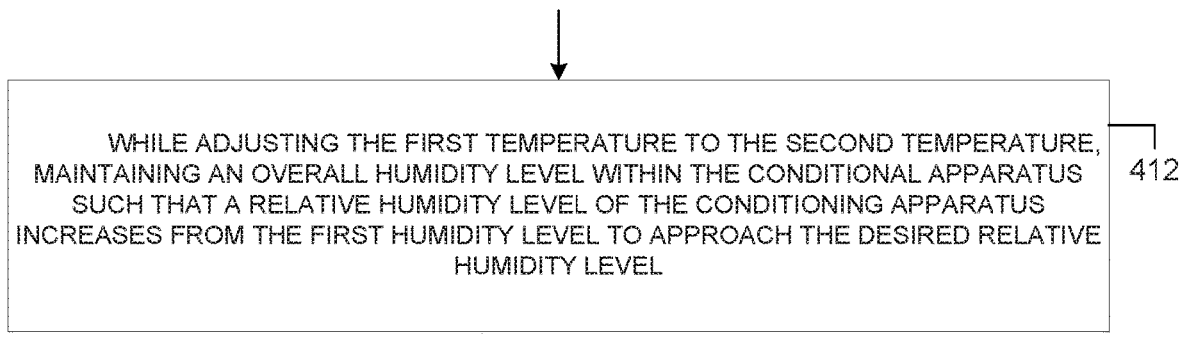
FIG. 6 illustrates a flowchart of a method for use with the method shown in FIG. 4, according to an example implementation.

FIG. 6 illustrates a flowchart of a method for use with the method 400 shown in FIG. 4, according to an example implementation. In particular, FIG. 6 illustrates the method 400 including block 412, and also may relate to functions shown in FIG. 5. Block 412 can relate to examples in which the desired relative humidity level is between 80% and 90%. At block 412, the method 400 includes, while adjusting the first temperature to the second temperature, maintaining an overall humidity level within the conditioning apparatus 112 such that a relative humidity level of the conditioning apparatus 112 increases from the first humidity level to approach the desired relative humidity level. Maintaining the overall humidity level in this manner may prevent the inner core layer from increasing moisture absorption beyond the desired relative humidity level.

Figure 7:
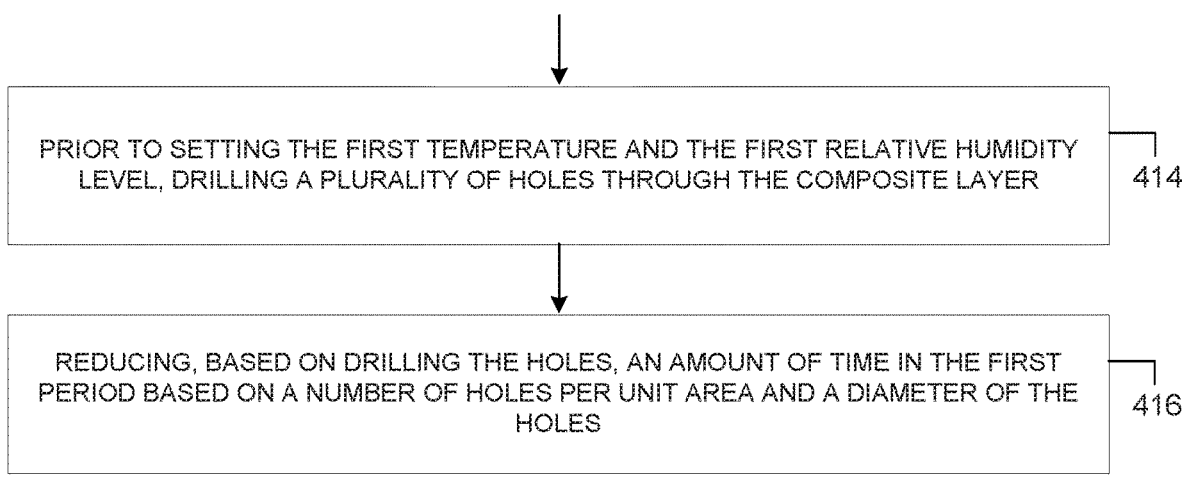
FIG. 7 illustrates a flowchart of a method for use with the method shown in FIG. 4, according to an example implementation.

FIG. 7 illustrates a flowchart of a method for use with the method 400 shown in FIG. 4, according to an example implementation. In particular, FIG. 7 illustrates the method 400 including blocks 414 and 416. At block 414, the method 400 includes, prior to setting the first temperature and the first relative humidity level, drilling a plurality of holes 302 through the outer composite layer. For example, the controller 102 may control a drilling apparatus to drill the plurality of holes 302 as shown in FIG. 3, or in accordance with another predetermined pattern. In other examples, this may involve receiving, by way of the user interface 110, an indication of the materials and configuration of the composite core sandwich coupon 200. At block 416, the method 400 further includes reducing, based on drilling the holes 302, an amount of time in the first period based on a number of holes per unit area and a diameter of the holes 302. For example, a higher concentration of holes and wider diameters may be inversely proportional to the amount of time in the first period.

Figure 8:
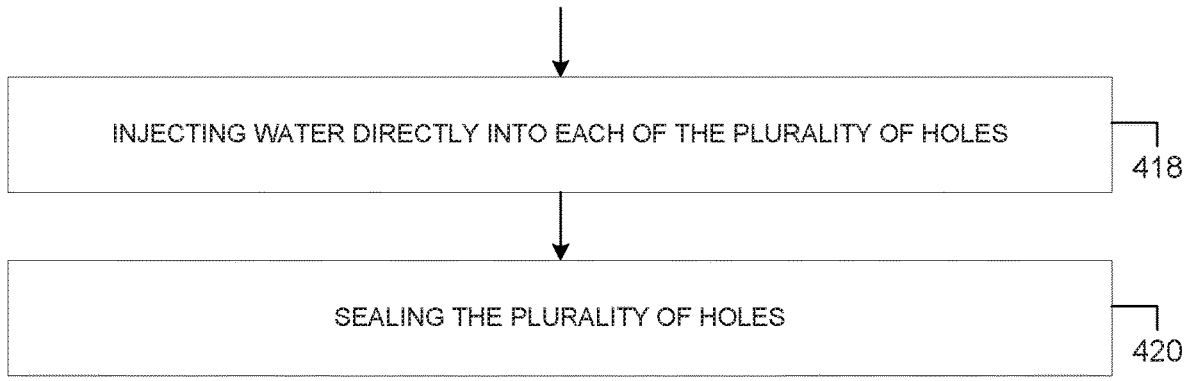
FIG. 8 illustrates a flowchart of a method for use with the method shown in FIG. 4, according to an example implementation.

FIG. 8 illustrates a flowchart of a method for use with the method 400 shown in FIG. 4, according to an example implementation. In particular, FIG. 8 illustrates the method 400 including blocks 418 and 420, and may further relate to functions shown in FIG. 7. At block 418, the method 400 includes injecting water directly into each of the plurality of holes 302. At block 420, the method 400 further includes sealing the plurality of holes. In this manner, at least some moisture absorbed by the inner core layer may come from the injected water, and not from the first relative humidity level. In further examples, substantially all of the absorbed moisture comes from the injected water, and, during the first period, the relative humidity level plays only a nominal role in conditioning the inner core material during the first period.

Figure 9:
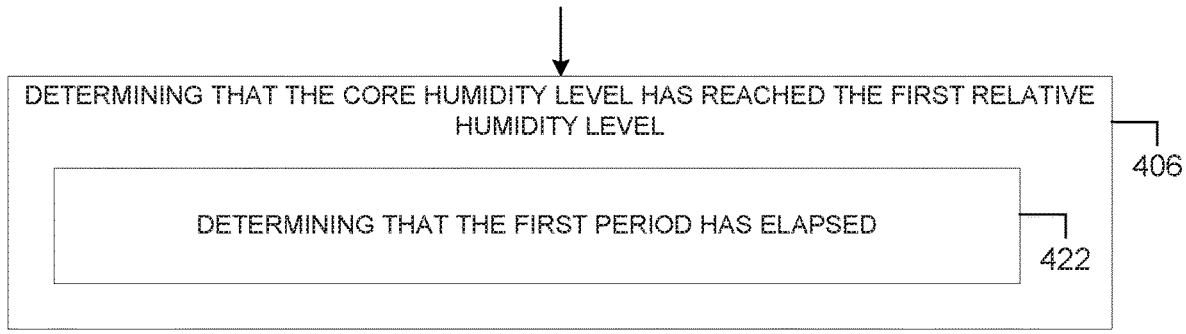
FIG. 9 illustrates a flowchart of a method for use with the method shown in FIG. 4, according to an example implementation.

FIG. 9 illustrates a flowchart of a method for use with the method 400 shown in FIG. 4, according to an example implementation. In particular, FIG. 9 illustrates the method 400 including block 422. Block 422 is performed in accordance with block 406. At block 422, the method 400 includes determining that the first period has elapsed. For example, the first period may be predetermined based on past conditioning data or an expected period calculated based on materials and configurations of the composite core sandwich coupon 200 (e.g., thicknesses of layers).

Figure 10:
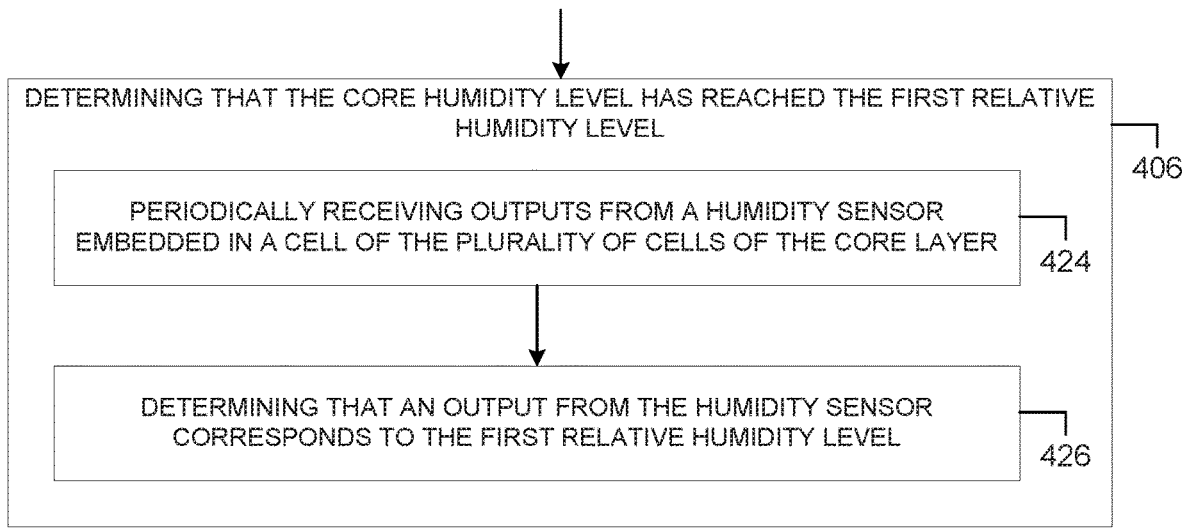
FIG. 10 illustrates a flowchart of a method for use with the method shown in FIG. 4, according to an example implementation.

FIG. 10 illustrates a flowchart of a method for use with the method 400 shown in FIG. 4, according to an example implementation. In particular, FIG. 10 illustrates the method 400 including blocks 424 and 426. Blocks 424 and 426 are performed in accordance with block 406. At block 424, the method 400 includes periodically receiving outputs from the humidity sensor 120 embedded in a cell of the plurality of cells of the core layer. At block 426, the method 400 includes determining that an output from the humidity sensor 120 corresponds to the first relative humidity level. For example, the output may be periodically sampled and compared to the first relative humidity level until the output matches the first relative humidity level.

Figure 11:
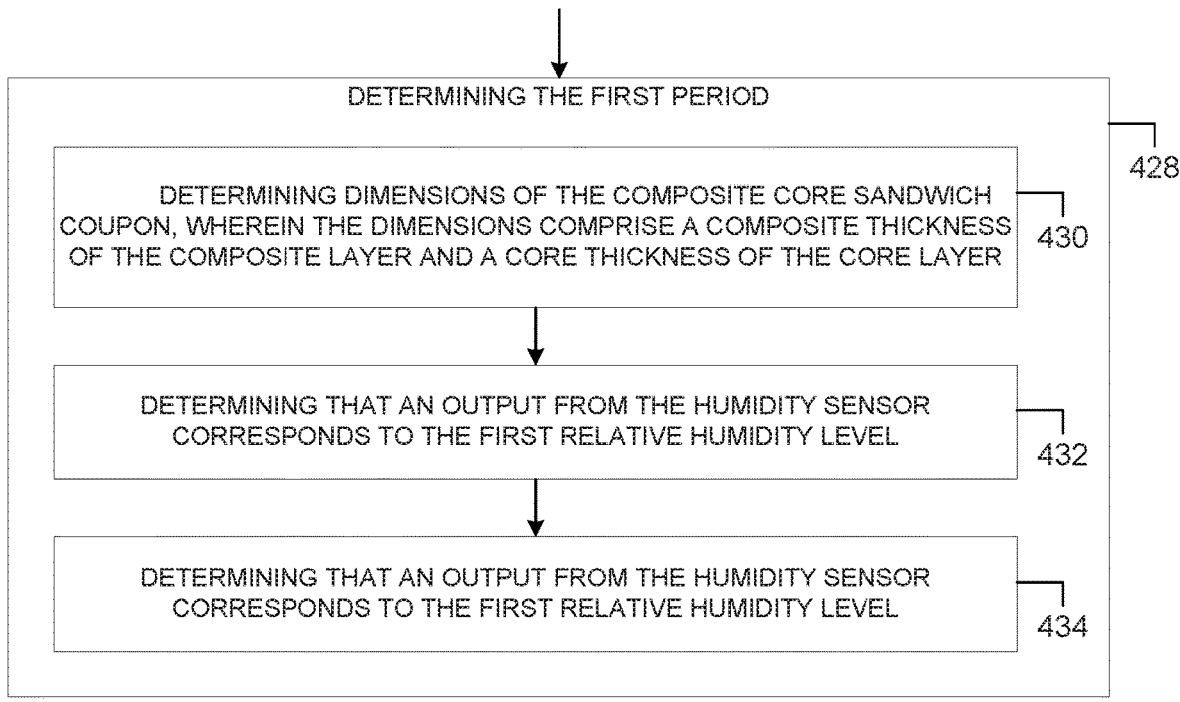
FIG. 11 illustrates a flowchart of a method for use with the method shown in FIG. 4, according to an example implementation.

FIG. 11 illustrates a flowchart of a method for use with the method 400 shown in FIG. 4, according to an example implementation. In particular, FIG. 11 illustrates the method 400 including blocks 428-434. At block 428, the method 400 includes determining the first period. Block 430, 432, and 434 are performed in accordance with FIG. 428. At block 430, the method 400 includes determining dimensions of the composite core sandwich coupon 200. The dimensions include a composite thickness of the composite layer and a core thickness of the core layer. For example, these dimensions may be determined based on providing input prompts at the user interface 110 and receiving corresponding inputs from the user interface 110. At block 432, the method 400 includes determining a core material. For example, the core material may be determined based on providing input prompts at the user interface 110 and receiving corresponding inputs from the user interface 110. Alternatively, the core material may be determined based on a project number or aircraft type associated with the composite core sandwich coupon 200. At block 434, the method 400 includes determining the first period based on a known humidity uptake characteristic of the core material and the core thickness. For example, the computing device may access a database or use the memory 106 to determine the known humidity uptake characteristic of the core material, and apply the humidity uptake characteristic to a volume of the core material determined based on the core thickness.

Figure 12:
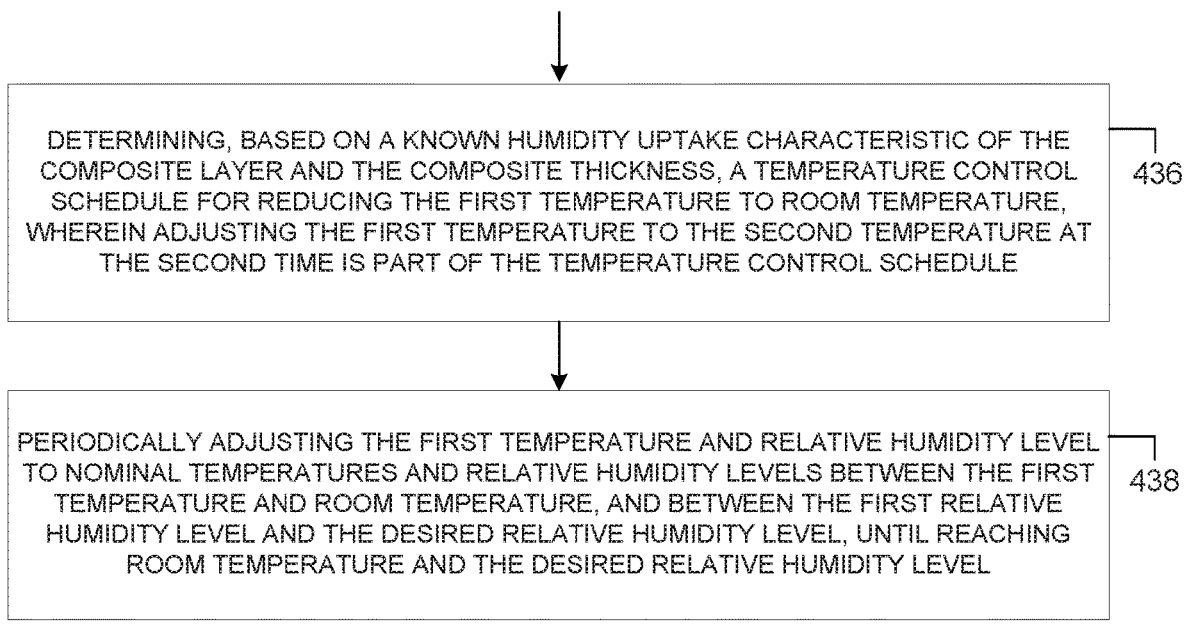
FIG. 12 illustrates a flowchart of a method for use with the method shown in FIG. 4, according to an example implementation.

FIG. 12 illustrates a flowchart of a method for use with the method 400 shown in FIG. 4, according to an example implementation. In particular, FIG. 12 illustrates the method 400 including blocks 436 and 438, and may relate to the functions shown in FIG. 11. At block 436, the method 400 includes determining, based on a known humidity uptake characteristic of the composite layer and the composite thickness, a temperature control schedule for reducing the first temperature to room temperature. For example, this may be carried out by the controller 102. In these examples, adjusting the first temperature to the second temperature at the second time is part of the temperature control schedule. At block 438, the method 400 includes periodically adjusting the first temperature and relative humidity level to nominal temperatures and relative humidity levels between the first temperature and room temperature, and between the first relative humidity level and the desired relative humidity level, until reaching room temperature and the desired relative humidity level. For example, this may involve iteratively changing the temperature and humidity level in an enclosure of the conditioning apparatus 112 until reaching room temperature and the desired relative humidity level. This may further involve maintaining an overall moisture level within the enclosure as the relative humidity levels change.

Figure 13:
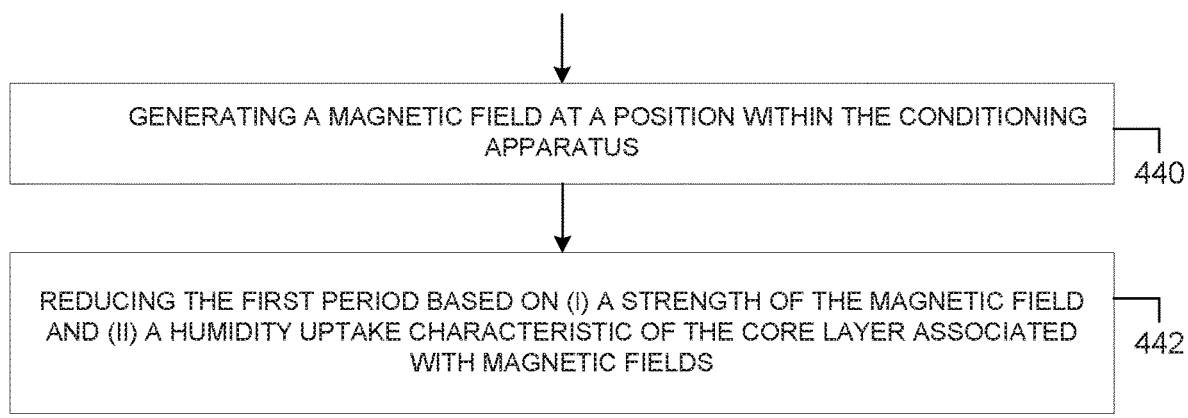
FIG. 13 illustrates a flowchart of a method for use with the method shown in FIG. 4, according to an example implementation.

FIG. 13 illustrates a flowchart of a method for use with the method 400 shown in FIG. 4, according to an example implementation. In particular, FIG. 13 illustrates the method 400 including blocks 440 and 442. At block 440, the method 400 includes generating a magnetic field at a position within the conditioning apparatus 112. For example, an electromagnet may be positioned within an enclosure of the conditioning apparatus and the controller 102 may be used to control the magnetic field of the electromagnet. At block 442, the method 400 includes reducing the first period based on (i) a strength of the magnetic field and (ii) a humidity uptake characteristic of the core layer associated with magnetic fields. For example, the humidity uptake characteristic of the core layer associated with magnetic fields may include data from past conditioning of coupons using the magnetic field. In this manner, systems for conditioning the composite core sandwich coupon 200 can more rapidly and predictably (due to the direction of the magnetic field lines) absorb moisture and thereby experience accelerated conditioning.

Figure 14:
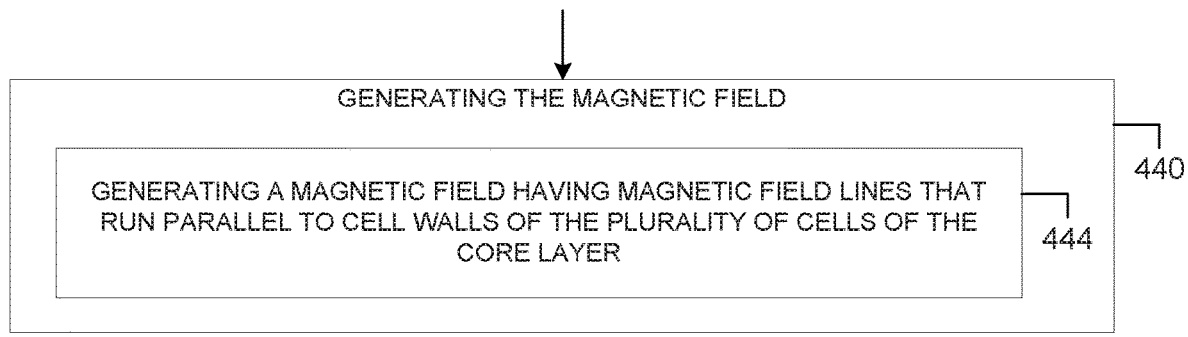
FIG. 14 illustrates a flowchart of a method for use with the method shown in FIG. 4, according to an example implementation.

FIG. 14 illustrates a flowchart of a method for use with the method 400 shown in FIG. 4, according to an example implementation. In particular, FIG. 14 illustrates the method 400 including block 444, and may relate to the functions shown in FIG. 13. At block 444, the method 400 includes generating a magnetic field having magnetic field lines that run parallel to cell walls of the plurality of cells of the core layer.

Thus, systems and method described herein use various means for reducing the time required to condition a coupon, particularly composite core sandwich coupons. These functions also increase the reliability and predictability of conditioning coupons and therefore result in materials that are more accurate in testing contexts. Further, performance of systems (such as an aircraft) can be improved at the end of an expected useful lifespan and over-engineering can be reduced by employing the methods and systems described herein.

By the term "substantially," "similarity," and "about" used herein, it is meant that the recited characteristic, parameter, or value need not be achieved exactly, but that deviations or variations, including for example, tolerances, measurement error, measurement accuracy limitations and other factors known to skill in the art, may occur in amounts that do not preclude the effect the characteristic was intended to provide.

Different examples of the system(s), device(s), and method(s) disclosed herein include a variety of components, features, and functionalities. It should be understood that the various examples of the system(s), device(s), and method(s) disclosed herein may include any of the components, features, and functionalities of any of the other examples of the system(s), device(s), and method(s) disclosed herein in any combination or any sub-combination, and all of such possibilities are intended to be within the scope of the disclosure.

The description of the different advantageous arrangements has been presented for purposes of illustration and description, and is not intended to be exhaustive or limited to the examples in the form disclosed. Many modifications and variations will be apparent to those of ordinary skill in the art. Further, different advantageous examples may describe different advantages as compared to other advantageous examples. The example or examples selected are chosen and described in order to best explain the principles of the examples, the practical application, and to enable others of ordinary skill in the art to understand the disclosure for various examples with various modifications as are suited to the particular use contemplated.

What is claimed is:

1. A method for accelerated conditioning of a composite core sandwich coupon within a conditioning apparatus, wherein the composite core sandwich coupon comprises (i) an outer composite layer and (ii) an inner core layer, and wherein the inner core layer comprises a plurality of cells, the method comprising:

creating a plurality of holes through the outer composite layer;

setting, at a first time by a controller of the conditioning apparatus after creating the plurality of holes, a first temperature of the conditioning apparatus between 140 and 180 degrees Fahrenheit and a first relative humidity level of the conditioning apparatus between 5% and 9%, and wherein a combination of the first temperature and the first relative humidity level correspond to a desired relative humidity level of the plurality of cells of the inner core layer at room temperature;

maintaining, by the controller, the first temperature and the first relative humidity level for a first period, wherein during the first period a core humidity of the plurality of cells in the inner core layer approaches the first relative humidity level;

determining that the core humidity has reached the first relative humidity level; and based on determining that the core humidity has reached the first relative humidity level, adjusting, at a second time by the controller of the conditioning apparatus, the first temperature to a second temperature, wherein the second temperature is between the first temperature and room temperature, and wherein, responsive to adjusting the first temperature to the second temperature, the outer composite layer absorbs moisture from the inner core layer to approach the desired relative humidity level.

2. The method of claim 1, wherein the desired relative humidity level is between 80% and 90%, the method further comprising, while adjusting the first temperature to the second temperature, maintaining an overall humidity level within the conditioning apparatus such that a relative humidity level of the conditioning apparatus increases from the first relative humidity level to approach the desired relative humidity level.

3. The method of claim 1, further comprising:
reducing, based on creating the plurality of holes, an amount of time in the first period based on a number of holes per unit area and a diameter of the holes.

4. The method of claim 1, further comprising:
placing water directly into each of the plurality of holes; and
sealing the plurality of holes.

5. The method of claim 1, wherein determining that the core humidity has reached the first relative humidity level comprises determining that the first period has elapsed.

6. The method of claim 1, wherein determining that the core humidity has reached the first relative humidity level comprises:
periodically receiving outputs from a humidity sensor embedded in a cell of the plurality of cells of the inner core layer; and
determining that an output from the humidity sensor corresponds to the first relative humidity level.

7. The method of claim 1, further comprising determining the first period, wherein determining the first period comprises:
determining dimensions of the composite core sandwich coupon, wherein the dimensions comprise a composite thickness of the outer composite layer and a core thickness of the inner core layer;
determining a core material; and
determining the first period based on a known humidity uptake characteristic of the core material and the core thickness.

8. The method of claim 7, further comprising:
determining, based on a known humidity uptake characteristic of the outer composite layer and the composite thickness, a temperature control schedule for reducing the first temperature to room temperature, wherein adjusting the first temperature to the second temperature at the second time is part of the temperature control schedule; and
periodically adjusting the first temperature and relative humidity level to nominal temperatures and relative humidity levels between the first temperature and room temperature, and between the first relative humidity level and the desired relative humidity level, until reaching room temperature and the desired relative humidity level.

9. The method of claim 1, further comprising:
generating a magnetic field at a position within the conditioning apparatus; and
reducing the first period based on (i) a strength of the magnetic field and (ii) a humidity uptake characteristic of the inner core layer associated with magnetic fields.

10. The method of claim 9, wherein generating the magnetic field comprises generating a magnetic field having magnetic field lines that run parallel to cell walls of the plurality of cells of the inner core layer.

11. The method of claim 1, wherein creating the plurality of holes comprises drilling the plurality of holes.

12. A system for accelerated conditioning of a composite core sandwich coupon comprising:
a conditioning apparatus having a chamber configured to contain a composite core sandwich coupon, wherein the composite core sandwich coupon comprises (i) an outer composite layer and (ii) an inner core layer, and wherein the inner core layer comprises a plurality of cells;
a humidifier configured to provide water vapor to the chamber of the conditioning apparatus;
a drilling apparatus;
a heater configured to provide heat to the chamber of the conditioning apparatus; and
a computing device comprising a processor and a memory having instructions executable by the processor to perform a set of functions, the set of functions comprising:
controlling the drilling apparatus to drill a plurality of holes through the outer composite layer;
controlling, after drilling the plurality of holes, the heater to set a first temperature of the conditioning apparatus between 140 and 180 degrees Fahrenheit and controlling the humidifier to set a first relative humidity level of the conditioning apparatus between 5% and 9%, and wherein a combination of the first temperature and the first relative humidity level correspond to a desired relative humidity level of the plurality of cells of the inner core layer at room temperature;

controlling the heater to maintain the first temperature and controlling the humidifier to maintain the first relative humidity level for a first period, wherein during the first period a core humidity of the plurality of cells in the inner core layer approaches the first relative humidity level;

determining that the core humidity has reached the first relative humidity level; and based on determining that the core humidity has reached the first relative humidity level, causing the heater to adjust, at a second time, the first temperature to a second temperature, wherein the second temperature is between the first temperature and room temperature, and wherein, responsive to adjusting the first temperature to the second temperature, the outer composite layer absorbs moisture from the inner core layer to approach the desired relative humidity level.

13. The system of claim 12, wherein controlling the heater to set the first temperature and controlling the humidifier to set the first relative humidity level comprises controlling the heater to set the first temperature to about 160 degrees Fahrenheit and controlling the humidifier to set the first relative humidity level to about 7%.

14. The system of claim 12, further comprising:
a humidity sensor embedded in a cell of the plurality of cells of the inner core layer, wherein determining that the core humidity has reached the first relative humidity level comprises:
periodically receiving outputs from the humidity sensor; and
determining that an output from the humidity sensor corresponds to the first relative humidity level.

15. The system of claim 12, wherein the computing device comprises a user interface, and wherein the set of functions further comprises:
receiving, by way of the user interface, an indication of (i) a material type of the outer composite layer, (ii) a material type of the inner core layer, and (iii) layer thicknesses and configurations of the composite core sandwich coupon; and
determining the first period based on receiving the indication of (i) the material type of the outer composite layer, (ii) the material type of the inner core layer, and (iii) the layer thicknesses and configurations of the composite core sandwich coupon.

16. The system of claim 12, further comprising an electromagnet, wherein the set of functions further comprises:
controlling the electromagnet to generate a magnetic field at a position within the conditioning apparatus; and
reducing the first period based on (i) a strength of the magnetic field and (ii) a humidity uptake characteristic of the inner core layer associated with magnetic fields.

17. The system of claim 16, wherein generating the magnetic field comprises generating a magnetic field having magnetic field lines that run parallel to cell walls of the plurality of cells of the inner core layer.

18. The system of claim 12, the set of functions further comprising:
reducing the first period based on the plurality of holes.

19. A non-transitory computer readable medium having stored thereon instructions, that when executed by one or more processors of a computing device, cause the computing device to perform functions for accelerated conditioning of a composite core sandwich coupon within a conditioning apparatus, wherein the composite core sandwich coupon comprises (i) an outer composite layer and (ii) an inner core layer, and wherein the inner core layer comprises a plurality of cells, the functions comprising:
creating, via a drilling apparatus, a plurality of holes through the outer composite layer;
setting, at a first time by a controller of the conditioning apparatus after creating the plurality of holes, a first temperature of the conditioning apparatus between 140 and 180 degrees Fahrenheit and setting a first relative humidity level of the conditioning apparatus between 5% and 9%, and wherein a combination of the first temperature and the first relative humidity level correspond to a desired relative humidity level of the plurality of cells of the inner core layer at room temperature;
maintaining, by the controller, the first temperature and the first relative humidity level for a first period, wherein during the first period a core humidity of the plurality of cells in the inner core layer approaches the first relative humidity level;
determining that the core humidity has reached the first relative humidity level; and
based on determining that the core humidity has reached the first relative humidity level, adjusting, at a second time by the controller of the conditioning apparatus, the first temperature to a second temperature, wherein the second temperature is between the first temperature and room temperature, and wherein, responsive to adjusting the first temperature to the second temperature, the outer composite layer absorbs moisture from the inner core layer to approach the desired relative humidity level.

20. The non-transitory computer readable medium of claim 19, wherein the desired relative humidity level is between 80% and 90%, the functions further comprising, while adjusting the first temperature to the second temperature, maintaining an overall humidity level within the conditioning apparatus such that a relative humidity level of the conditioning apparatus increases from the first relative humidity level to approach the desired relative humidity level.

* * * * *